(12) United States Patent
Park

(10) Patent No.: US 12,320,805 B2
(45) Date of Patent: Jun. 3, 2025

(54) SIMPLE DISEASE DIAGNOSIS TOOL

(71) Applicant: Dong Jin Park, Gwangju (KR)

(72) Inventor: Dong Jin Park, Gwangju (KR)

(*) Notice: Subject to any disclaimer, the term of this patent is extended or adjusted under 35 U.S.C. 154(b) by 604 days.

(21) Appl. No.: 17/788,414

(22) PCT Filed: Dec. 17, 2020

(86) PCT No.: PCT/KR2020/018515
§ 371 (c)(1),
(2) Date: Jun. 23, 2022

(87) PCT Pub. No.: WO2021/137484
PCT Pub. Date: Jul. 8, 2021

(65) Prior Publication Data
US 2023/0032700 A1    Feb. 2, 2023

(30) Foreign Application Priority Data
Jan. 2, 2020    (KR) .................. 10-2020-0000519

(51) Int. Cl.
*G01N 33/543*    (2006.01)
*B01L 3/00*    (2006.01)

(52) U.S. Cl.
CPC ...... *G01N 33/54388* (2021.08); *B01L 3/5023* (2013.01); *B01L 2200/16* (2013.01); *B01L 2300/0803* (2013.01); *B01L 2300/0825* (2013.01); *B01L 2300/161* (2013.01)

(58) Field of Classification Search
CPC ....... G01N 33/54388; G01N 33/54393; G01N 33/689; G01N 33/6893; G01N 33/54386; G01N 33/558; B01L 3/5023; B01L 2200/16; B01L 2300/0803; B01L 2300/0825; B01L 2300/161
See application file for complete search history.

(56) References Cited

U.S. PATENT DOCUMENTS

| | | | |
|---|---|---|---|
| 9,586,204 B2* | 3/2017 | Hong | B01L 3/5023 |
| 2008/0317633 A1* | 12/2008 | Sibbett | B01L 3/5023 156/247 |
| 2018/0148774 A1* | 5/2018 | Kim | C12Q 1/00 |

FOREIGN PATENT DOCUMENTS

| | | |
|---|---|---|
| JP | 2016-176938 A | 10/2016 |
| JP | 2018-021790 A | 2/2018 |
| KR | 10-2001-0076415 A | 8/2001 |
| KR | 10-2012-0046616 A | 5/2012 |
| KR | 10-2017-0134481 A | 12/2017 |
| KR | 10-2019-0067741 A | 6/2019 |

* cited by examiner

*Primary Examiner* — Dennis White
(74) *Attorney, Agent, or Firm* — NKL Law; Jae Youn Kim

(57) ABSTRACT

Proposed is a simple disease diagnosis tool including a base plate made of a material that is hydrophilic and spreads water sufficiently, and pattern display panels made of a material that is also hydrophilic and spreads water sufficiently and each adhered to one side surface of the base plate, wherein a reagent is applied to one side of the base plate, and wherein the pattern display panels include a plurality of disease test display portions each configured to have one end in contact with the reagent of the base plate or to be spaced apart from the reagent of the base plate by predetermined intervals, and diagnosis checking lines each marked to surround the outside of the disease test display portions while being spaced apart from the disease test display portions at predetermined intervals.

1 Claim, 7 Drawing Sheets

SIMPLE DISEASE DIAGNOSIS TOOL

TECHNICAL FIELD

The present invention relates to a simple disease diagnosis tool, and more particularly to a simple disease diagnosis tool that allows anyone to easily check whether he or she is infected with various diseases on his or her own and to check whether an appropriate diagnosis has been made.

BACKGROUND ART

Humankind has suffered from numerous diseases, and many people are dying from diseases. The main way to prevent death from these diseases is mentioned as diagnosing diseases rapidly.

However, many people do not want to spend a lot of time to receive disease diagnoses. The reality is that especially in the case of the pregnancy of minors and diseases such as AIDS, patients are reluctant to expose themselves to the outside, so that it is not easy to diagnose such diseases.

This has become a social problem because there are frequent cases of missing treatment time or failing to check whether infection is present, so that situations are worsened.

In addition, conventional disease diagnosis tools are disadvantageous in that they often require the help of others, cannot check whether an examinee is infected with various diseases at one time, and have a structure that does not allow whether a self-performed diagnosis has been appropriately made to be checked, so that it is difficult to have confidence in diagnosis.

RELATED ART LITERATURE

1. Korean Patent Application Publication No. 10-2012-0046616

DISCLOSURE

Technical Problem

An object of the present invention is to provide a novel disease diagnosis tool that prevents more people from dying from disease without undergoing medical treatment by promoting the diagnosis of disease by themselves rather than the diagnosis of disease by others that infringes on personal privacy, and is also to provide a novel disease diagnosis tool that has a simple structure like a pregnancy tester to make it easier to understand the tool and can be manufactured at a low cost, so that various diseases can be diagnosed with a single test and whether a self-diagnosis has been appropriately made can be checked.

Technical Solution

In order to accomplish the above object, an embodiment of the present invention provides a simple disease diagnosis tool including a base plate made of a material that is hydrophilic and spreads water sufficiently, and pattern display panels made of a material that is also hydrophilic and spreads water sufficiently and each adhered to one side surface of the base plate, wherein a reagent is applied to one side of the base plate, and wherein the pattern display panels include a plurality of disease test display portions each configured to have one end in contact with the reagent of the base plate or to be spaced apart from the reagent of the base plate by predetermined intervals, and diagnosis checking lines each marked to surround the outside of the disease test display portions while being spaced apart from the disease test display portions at predetermined intervals.

According to an embodiment of the present invention, the materials of the base plate and the pattern display plates are made of hydrophilic pulp, the pattern display plates are formed to be attached to both sides of the base plate, respectively, and the plurality of disease test display portions are configured such that different disease test samples are applied to the plurality of disease test display portions, respectively, and check for different diseases.

According to an embodiment of the present invention, the plurality of disease test display portions is arranged in a circle around the reagent at the same intervals, or is arranged on the reagent at the same intervals in the same direction as the reagent extends, or in a sector form around the reagent at regular intervals.

According to an embodiment of the present invention, the disease test display portions and the diagnosis checking lines are formed on one corner or edge of each of the base plate and the pattern display plates, so that the other side of each of the base plate and the pattern display plates can be used as a grip portion.

Advantageous Effects

An effect of the above-described present invention is to allow a biomarker (urine, saliva, or the like secreted from a human) to be easily spread because the present invention includes the base plate made of a material that is hydrophilic and spreads water sufficiently and the pattern display plates made of a material that is also hydrophilic and spreads water sufficiently, thereby making it possible to rapidly and accurately diagnose diseases. In this case, pulp (tissue or toilet paper) that is hydrophilic and spreads water sufficiently is used as the materials, so that the manufacturing cost of the base plate and the pattern display panels is considerably inexpensive, which means that the present invention can be effectively used for low-income people or in underdeveloped countries.

Furthermore, in the present invention, the pattern display plates are formed on both sides of the base plate to which the reagent is applied, so that diagnosis using both the front and back of the base plate, i.e., the three-dimensional diagnosis of diseases, is possible.

Furthermore, in the present invention, the plurality of disease test display portions is in the state in which different disease test samples are applied thereto, so that various diseases, e.g., AIDS, diabetes, various cancers, pregnancy, and/or the like, can be diagnosed at one time with one biomarker i.e., one test.

Moreover, the present invention is a significantly useful invention in that the diagnosis checking lines are marked around the outside of the disease test display portions that can check whether there is disease from a biomarker and the disease test display portions react only to the reagent and change the color thereof, thereby clearly showing whether the biomarker has reached the disease test display portions together with the reagent, so that whether a diagnosis has been appropriately made can be checked with the naked eye.

BEST MODE

Figure 1:
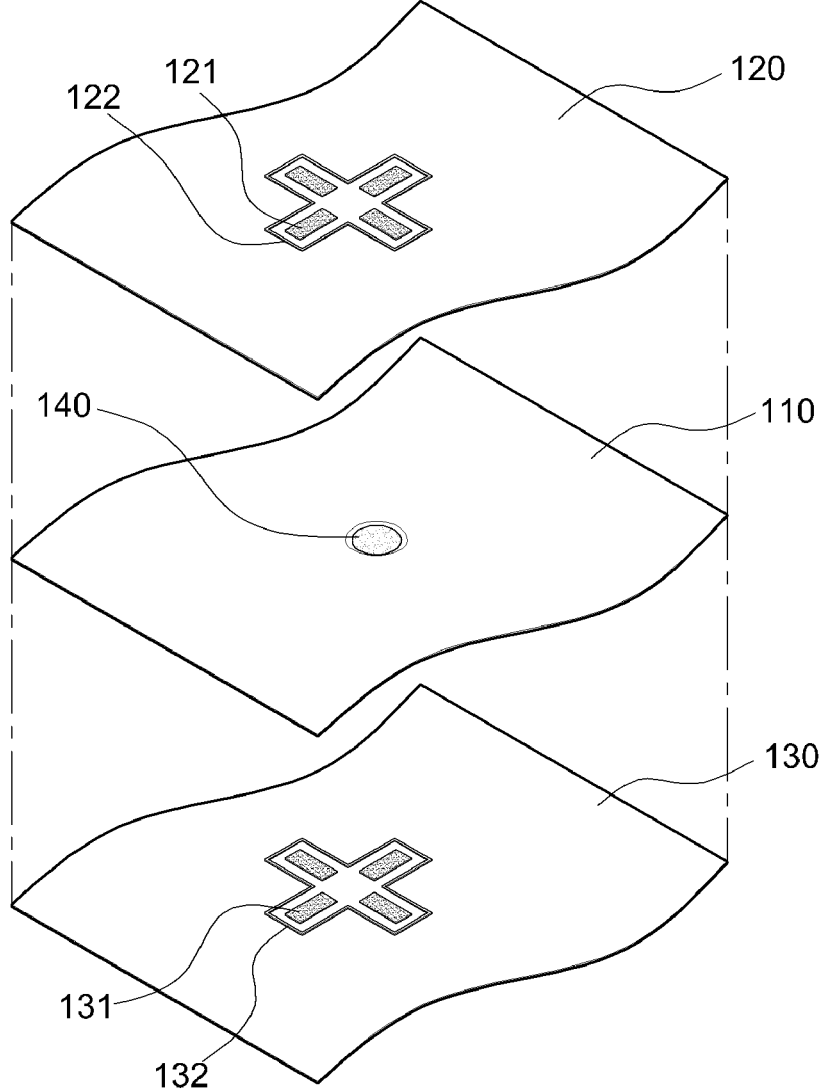
FIG. 1 is an exploded perspective view showing a simple disease diagnosis tool according to an embodiment of the present invention.

Embodiments of the present invention will be described in detail below with reference to the accompanying drawings so that those of ordinary skill in the art to which the present invention pertains can easily practice the present invention. However, the present invention may be embodied in several different forms and is not limited to the embodiments described herein. The terminology used herein is intended to refer to specific embodiments only, and is not intended to limit the invention. Furthermore, singular forms used herein include plural forms unless the phrases clearly indicate the opposite. The meaning of "comprising" used herein specifies a particular characteristic, region, integer, step, operation, element and/or component, and does not exclude the presence or addition of another specific characteristic, region, integer, step, operation, element, component, and/or group. Although not defined otherwise, all terms including technical terms and scientific terms used herein have the same meanings as commonly understood by those of ordinary skill in the art to which the present invention pertains. Commonly used terms defined in the dictionary are additionally interpreted as having meanings consistent with the related art literature and the currently disclosed content, and are not interpreted as having ideal or official meanings unless defined.

The embodiments of the present invention described with reference to perspective views specifically represent ideal embodiments of the present invention. As a result, various modifications of the illustrations, e.g., the modifications of a manufacturing method and/or specifications, are expected. Accordingly, the embodiments are not limited to the specific shapes of the illustrated areas, and include, e.g., the shapes deformed by manufacturing. For example, the regions shown or described as being flat may have characteristics that are generally rough/rough and non-linear. Furthermore, the portions shown as having sharp angles may be rounded. Therefore, the regions shown in the drawings are only approximate in nature, and their shapes are intended neither to depict the exact shapes of the regions nor to narrow the scope of the present invention.

Mode for Invention

Preferred embodiments of the present invention will be described in detail below with reference to the accompanying drawings.

Figure 2:
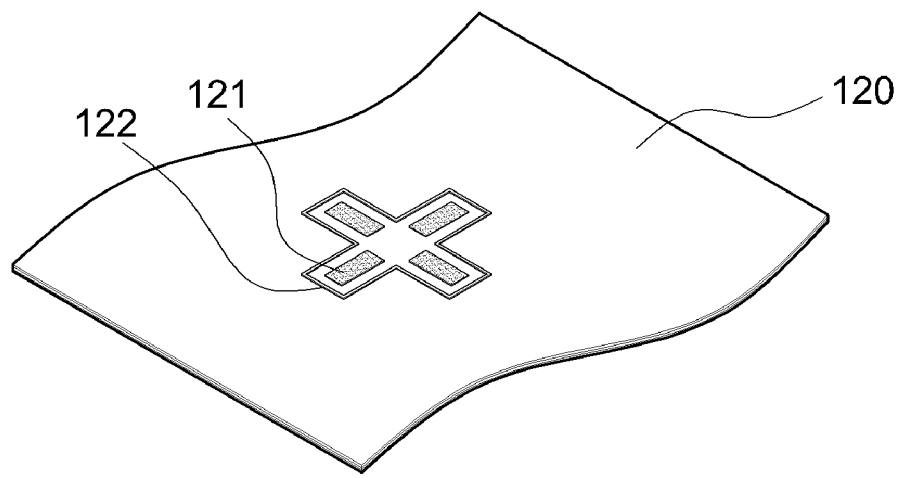
FIG. 2 is a perspective view showing the assembled state of FIG. 1.
Figure 3:
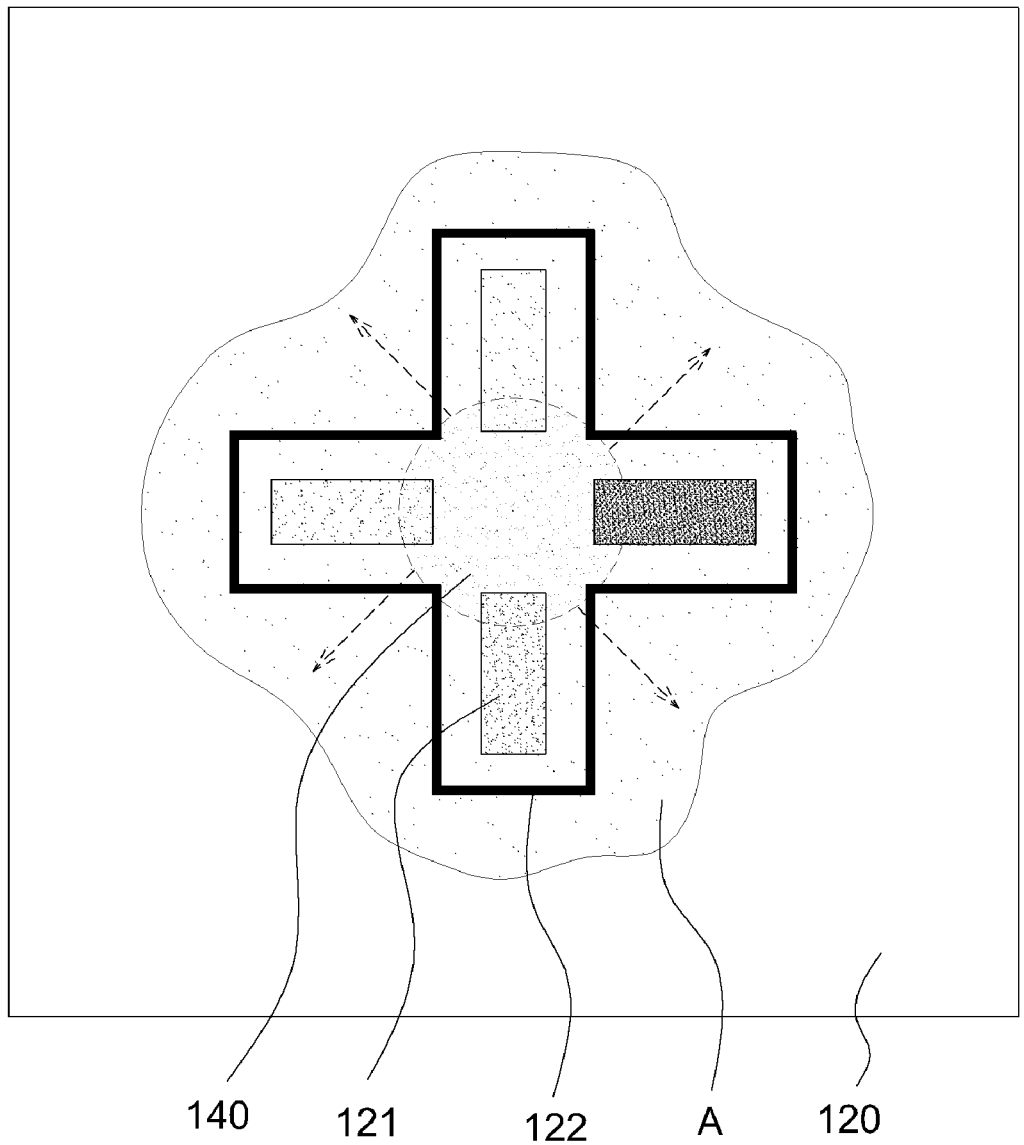
FIG. 3 is a reference view of the use state of the present invention.
Figure 4:
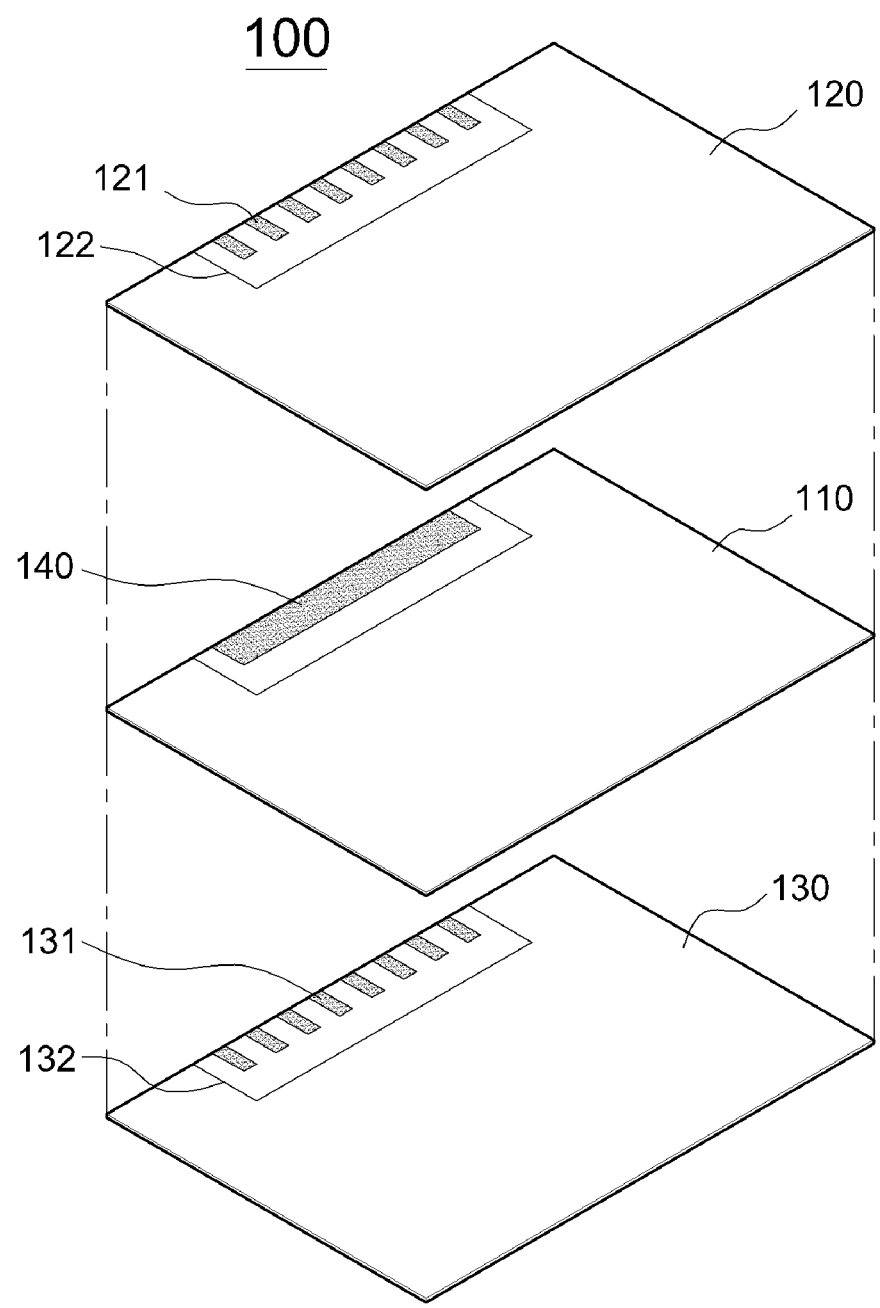
FIG. 4 is an exploded perspective view of another embodiment of the present invention.
Figure 5:
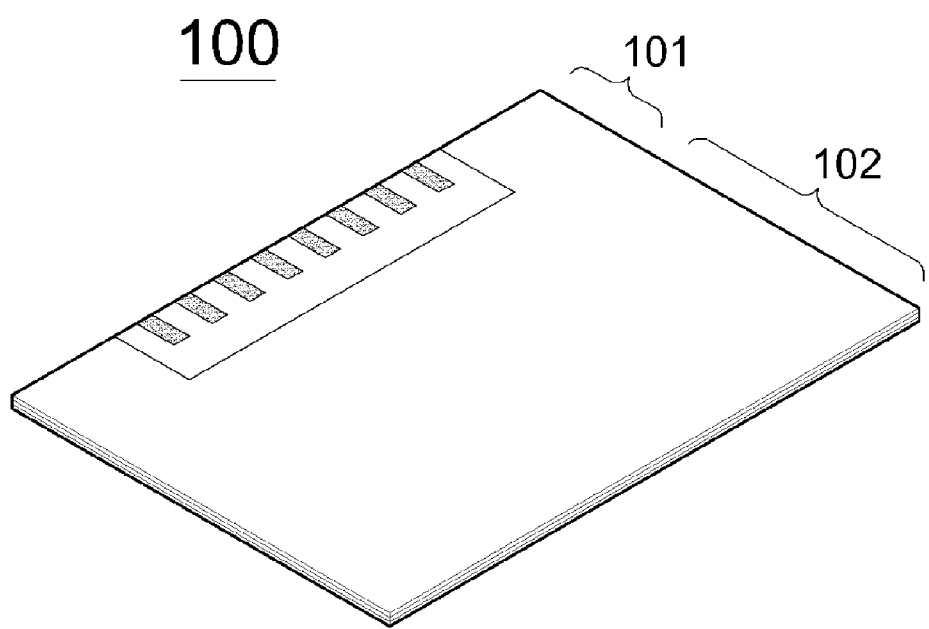
FIG. 5 is a perspective view showing the assembled state of FIG. 4.
Figure 6:
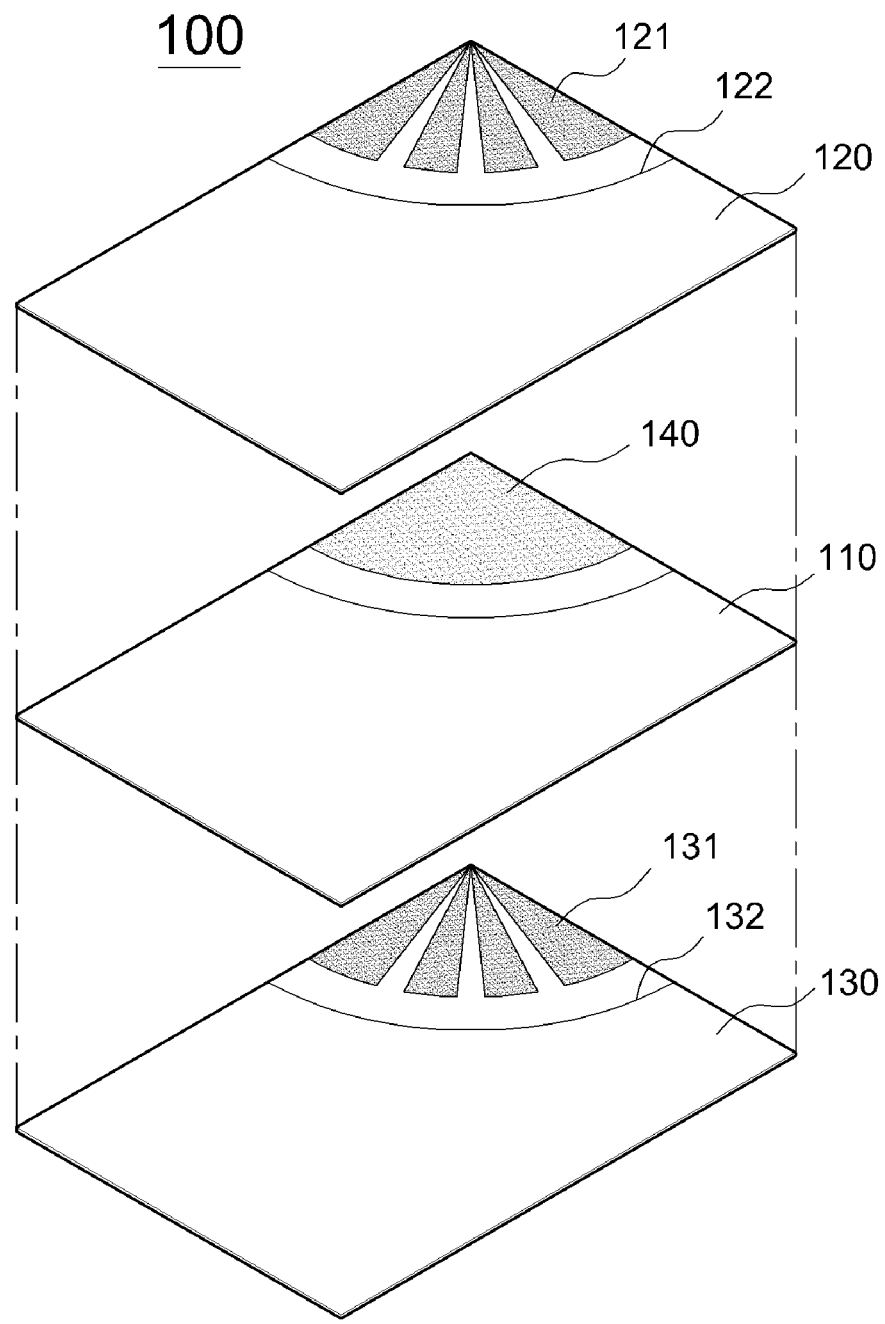
FIG. 6 is an exploded perspective view of still another embodiment of the present invention.
Figure 7:
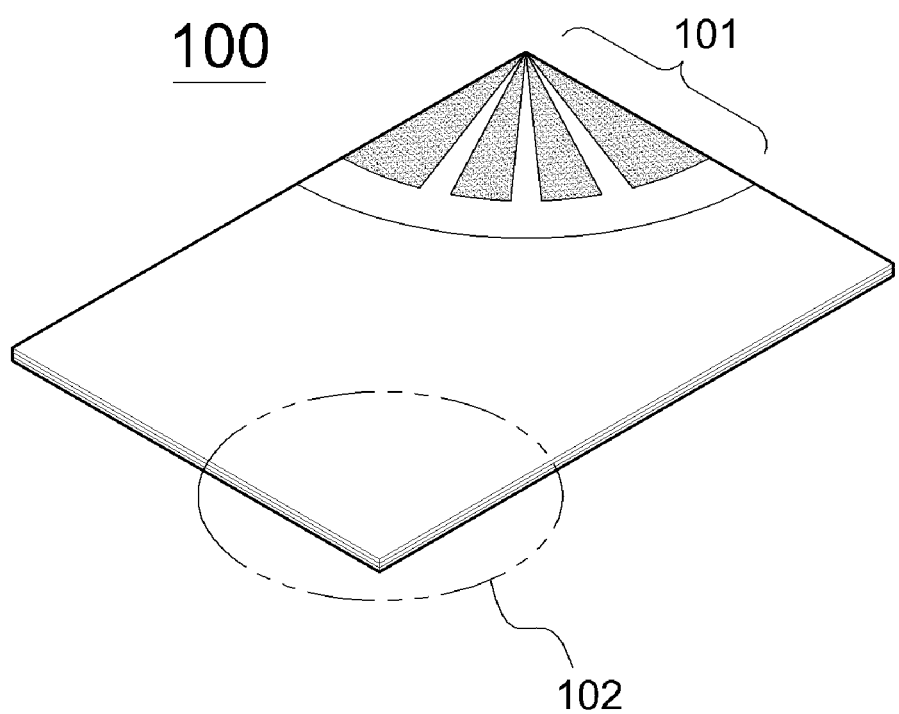
FIG. 7 is a perspective view showing the assembled state of FIG. 6.

FIG. 1 is an exploded perspective view showing a simple disease diagnosis tool according to an embodiment of the present invention, FIG. 2 is an assembled perspective view of FIG. 1, FIG. 3 is a reference view of the use state of the present invention, and FIG. 4 is an exploded perspective view of another embodiment of the present invention, FIG. 5 is a perspective view showing the assembled state of FIG. 4, FIG. 6 is an exploded perspective view of still another embodiment of the present invention, and FIG. 7 is a perspective view showing the assembled state of FIG. 6.

First, it should be noted that in the drawings, the same components or parts are denoted by the same reference numerals whenever possible. Furthermore, in the description of the present invention, a detailed description of a related well-known function or configuration will be omitted in order not to obscure the gist of the present invention.

The simple disease diagnosis tool 100 of the present invention includes a base plate 110 made of a material that is hydrophilic and spreads water sufficiently, and pattern display panels 120 and 130 made of a material that is also hydrophilic and spreads water sufficiently and each adhered to one side surface of the base plate 110. A reagent 140 is applied to the center portion of the base plate 110. The pattern display panels 120 and 130 include a plurality of disease test display portions 121 and 131 each configured to have one end in contact with the reagent 140 of the base plate 110 or to be spaced apart from the reagent 140 of the base plate 110 by predetermined intervals, and diagnosis checking lines 122 and 132 each marked to surround the outside of the disease test display portions 121 or 131 while being spaced apart from the disease test display portions 121 or 131 at predetermined intervals.

In this case, it is preferable to use hydrophilic pulp as the materials of the base plate 110 and the pattern display plates 120 and 130. As described above, the fact that pulp that is hydrophilic and spreads water sufficiently is used as the materials of the base plate 110 and the pattern display plates 120 and 130 means that the present invention may be manufactured at a low manufacturing cost like tissue or toilet paper.

As described above, when the material cost of the base plate 110 and the pattern display plates 120 and 130 becomes less inexpensive, the price of the disease diagnosis tool of the present invention also becomes less inexpensive. This means that the present invention may be used considerably effectively for the residents of poor, underdeveloped countries, etc. because the distribution thereof among them is easy.

In the present invention, the pattern display plates 120 and 130 may be configured to be formed on both sides of the base plate 110. The reason for this is that in this case, diagnosis results can be checked from both sides. This is a necessary configuration for the convenience of use and checking given that a rather unsanitary biomarker (urine, saliva, or the like secreted from a human) is used. It is obvious that the disease test display portions 121 and 131, to which disease test samples 121 and 131 are applied, and the diagnosis checking lines 122 and 132 are marked on the pattern display panels 120 and 130.

In addition, in the present invention, a plurality of disease test display portions 121 and 131 may be arranged around the reagent 140 at the same intervals. This allows different disease test samples to be applied to the disease test display portions 121 and 131, so that a configuration may be made such that a biomarker mixed with the reagent 140, i.e., an anti-body A, reacts to the individual disease test samples of the disease test display portions 121 and 131, thereby diagnosing different diseases.

For example, when test samples for diagnosing AIDS, diabetes, various cancers, pregnancy, and/or the like are applied to the disease test display portions 121 and 131, AIDS, diabetes, various cancers, and pregnancy may be identified with only one biomarker.

This provides a significantly convenient way to check whether an examinee has one of multiple diseases or is pregnant with a single test.

In addition, the present invention is configured to mark the diagnosis checking lines 122 and 132 so that they are spaced apart from the outside of the plurality of disease test display portions 121 and 131 at predetermined intervals. This is a configuration adapted to determine whether the anti-body A has reached the diagnosis checking line 122 or 132. The color of the diagnosis checking line 122 or 132 is configured to change when the anti-body A reaches the diagnosis checking line 122 or 132. Accordingly, it is preferable that the diagnosis checking lines 122 and 132 be coated with a component that allows the color thereof to change in response to the reagent 140.

When the color of the diagnosis checking line 122 or 132 changes in this way, it may be clearly determined that an examiner's biomarker has reliably reached the disease test display portion 121 or 131 together with the reagent 140. Accordingly, the examiner may determine whether his/her self-diagnosis has been appropriately made based on the change in the color of the disease test display portion 121 or 131 with the naked eye, and may then feel relieved. In this case, when four types of disease test samples are arranged around the reagent 140 at regular intervals, each of the diagnosis checking lines 122 and 132 will be represented in a shape that resembles the outline of a cross.

In the present invention, the pattern refers to the disease test display portions 121 and 131 and the diagnosis checking lines 122 and 132.

The views depicted in FIGS. 4 and 5 show another embodiment of the present invention. When the disease test display portions 121 and 131 and the diagnosis checking lines 122 and 132 are disposed in the center portions of the base plate 110 and the pattern display plates 120 and 130, the portion that can be held by a person, i.e., a grip portion 102, is narrow, thereby making it inconvenient to use the disease diagnosis tool.

Furthermore, it may not be easy to attach a biomarker such as saliva or urine to the disease test display portions 121 and 131.

Accordingly, in the present invention, a plurality of disease test display portions 121 and 131 and diagnosis checking lines 122 and 132 may be formed on one side edges of a base plate 110 and pattern display plates 120 and 130, and the other sides of the base plate 110 and the pattern display plates 120 and 130 may be used as grip portions 102.

In this case, it is preferable that the disease test display portions 121 and 131 be configured to be arranged on a reagent 140 at the same intervals in the same direction as the reagent 140 extends, like straight barcodes.

As described above, although the present invention has been described via the limited embodiments, the present invention is not limited thereto. Various modifications and variations may be made within the technical spirit of the present invention and equivalents of the claims to be described below by those of ordinary skill in the art to which the present invention pertains.

DESCRIPTION OF SYMBOLS

100: simple disease diagnosis tool of the present invention
101: test portion
102: grip portion
110: base plate
120: pattern display plate
121: disease test display portion
122: diagnosis checking line
130: pattern display plate
131: disease test display portion
132: diagnosis checking line
140: reagent
A: anti-body

The invention claimed is:

1. A simple disease diagnosis tool comprising a base plate made of a material that is hydrophilic and pattern display made of a material that is hydrophilic;
   and a grip portion is formed on one side of each of the base plate and the pattern display plates;
   wherein a reagent is applied to the base plate;
   wherein a plurality of disease test display portions arranged on each of the pattern display plates, and arranged such that when the pattern display plates are superimposed on the base plate, the disease test display portions are arranged in a circular form around the reagent so that one side end comes into contact with the reagent or spaced apart from the reagent at same intervals; and
   wherein diagnosis checking lines are marked to surround an outside of the disease test display portions while being spaced apart from the disease test display portions at predetermined intervals.

* * * * *